United States Patent [19]

Innes et al.

[11] 4,328,157

[45] May 4, 1982

[54] PRODUCTION OF MALEIC ANHYDRIDE

[75] Inventors: Robert A. Innes; Anthony J. Perrotta, both of Monroeville, Pa.

[73] Assignee: Gulf Research & Development Company, Pittsburgh, Pa.

[21] Appl. No.: 245,255

[22] Filed: Mar. 19, 1981

[51] Int. Cl.³ .................................. C07D 307/60
[52] U.S. Cl. .............................. 549/258; 252/470
[58] Field of Search ......................... 260/346.75

[56] References Cited

U.S. PATENT DOCUMENTS 4,113,745  9/1978  Strojny et al. ................. 260/346

Primary Examiner—Henry R. Jiles
Assistant Examiner—Bernard Dentz
Attorney, Agent, or Firm—Deane E. Keith; Forrest D. Stine; Joseph J. Carducci

[57] ABSTRACT

Maleic anhydride is produced by passing a $C_4$ to $C_{12}$ hydrocarbon stream together with molecular oxygen over a fixed bed containing a vanadium molybdate catalyst promoted with a novel cobalt niobate having the formula $$CoNb_aO_x$$

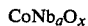

wherein a is a number from about 1.0 to about 4.0 and x is a number from about 3.5 to about 11.0. The catalyst is prepared by calcining a slurry containing cobalt oxide and niobium oxide, or their precursors, in at a temperature range from about 400° to about 1200° C. for about 1 to about 40 hours to obtain a cobalt niobate, which is then slurried with a mixture of oxides of vanadium and molybdenum, or their precursors, dried, and then calcined at a temperature from about 300° to about 650° C. for about 0.5 to about 24 hours. A support cam can be used for the catalyst.

23 Claims, No Drawings

PRODUCTION OF MALEIC ANHYDRIDE

CROSS REFERENCE TO RELATED APPLICATION

Reference is made to U.S. patent application Ser. No. 245,323 to R. A. Innes and A. J. Perrotta entitled "Cobalt Tantalate, Catalyst Promoted Therewith, Preparation Thereof, Production of Maleic Anhydride Using Said Catalyst" filed on even date, which application is hereby incorporated by reference.

FIELD OF THE INVENTION

The present invention relates to a novel cobalt niobate, a cobalt niobate-promoted catalyst, a method for preparing such catalyst and a process for producing improved yields of maleic anhydride using such catalyst. More particularly, the invention relates to a novel cobalt niobate, a vanadium molybdate catalyst promoted with cobalt niobate and to the production of maleic anhydride by oxidation of a $C_4$-$C_{12}$ hydrocarbon stream using a cobalt niobate-promoted vanadium molybdate catalyst.

DESCRIPTION OF THE PRIOR ART

The oxidation of hydrocarbons to produce maleic anhydride using a catalyst system comprising a vanadium oxide, a molybdenum oxide or mixtures thereof is well known. More recently, such catalyst systems have included materials in addition to the vanadium and/or molybdenum oxides, e.g., phosphorous, silica or titanium, and are discussed in U.S. Pat. No. 4,113,745 entitled "Catalyst for and Method of Producing Maleic Anhydride" to Strojny et al, which describes a process for obtaining maleic anhydride wherein a $C_5$ hydrocarbon stream is oxidized with an oxygen-containing gas over a catalyst mixture containing 30 to 60 weight percent vanadium oxide, 5 to 40 weight percent molybdenum oxide and 25 to 60 weight percent titanium oxide on an alpha alumina or alumina silica support having a surface area of less than one square meter per gram. The presence of titanium oxide in selected amounts in the catalyst apparently results in higher maleic anhydride yields and permits slightly lower temperatures during the reaction.

SUMMARY OF THE INVENTION

A cobalt niobate-promoted vanadium molybdate catalyst has now been found which provides improved yields of maleic anhydride from the vapor phase reaction of a hydrocarbon stream with molecular oxygen. Thus, the cobalt niobate-promoted vanadium molybdate catalyst of the present invention can provide higher yields of maleic anhydride than are obtained using a titanium dioxide-promoted vanadium molybdate catalyst.

The catalyst of the present invention comprises a mixture of vanadium oxides and molybdenum oxides, herein referred to as "vanadium molybdate," promoted with a novel cobalt niobate composition having the formula:

$$CoNb_aO_x$$

wherein a is a number in the range from about 1.0 to about 4.0, and x is a number in the range from about 3.5 to about 11.0. The cobalt niobate can be a single crystalline phase having the formula $CoNb_2O_6$ or can be a combination of crystalline phases. On an elemental basis, the molar ratio of vanadium to molybdenum can be in the range of about 2:1 to about 10:1. The weight ratio of the vanadium molybdate to the cobalt niobate can be in the range of about 1:3 to about 3:1.

The cobalt niobate-promoted catalyst of the present invention is prepared by calcining an admixture of a cobalt compound with a niobium compound in the presence of an oxygen-containing gas to produce the desired cobalt niobate. Calcination of the cobalt niobate must be conducted at a temperature in the range of between 400° to about 1200° C. to obtain a highly active catalyst for the production of maleic anhydride. The resulting cobalt niobate is mixed with a vanadium compound and a molybdenum compound, and the mixture is then calcined in the presence of an oxygen-containing gas at a temperature in the range of between about 300° to about 650° C.

The process of the present invention comprises passing a vaporous mixture comprising at least one $C_4$ to $C_{12}$ hydrocarbon and molecular oxygen at elevated temperature and pressure over the cobalt niobate-promoted catalyst to produce high yields of maleic anhydride.

DESCRIPTION OF THE PREFERRED EMBODIMENTS

As previously indicated, the catalyst of the present invention is promoted with a novel cobalt niobate of the formula:

$$CoNb_aO_x$$

wherein a is a number ranging from about 1.0 to about 4.0, preferably from about 1.5 to about 3.0, and x is a number ranging from about 3.5 to about 11.0, preferably from about 4.5 to about 8.5. The molar ratio of vanadium to molybdenum can be in the range of about 2:1 to about 10:1, preferably about 3:1 to about 7:1 on an elemental basis. The weight ratio of the vanadium molybdate to the cobalt niobate can be in the range of about 1:3 to about 3:1, preferably about 1:2 to about 2:1.

The novel cobalt niobate promoter is prepared by calcining a mixture of a cobalt compound and a niobium compound in the presence of a molecular oxygen-containing gas, such as air, substantially pure oxygen or the like, at a temperature in the range of about 400° to about 1200° C., preferably from about 450° to about 700° C., for about 1 to about 40 hours, preferably from about 8 to about 24 hours. Any suitable pressure can be employed, since calcination pressure is not critical. Thus, the pressure can be as high as desired, for example, up to about 50 pounds per square inch gauge (345 kPa) or even higher. However, atmospheric pressure is preferred. The aforesaid calcination temperatures must be utilized to produce a highly active catalyst. As a result of such calcination, the cobalt niobate forms crystalline phases that render the final catalyst extremely effective for obtaining high maleic anhydride yields.

Suitable cobalt and niobium compounds include, for example, cobalt oxide, niobium oxide and compounds which form such oxides under calcination conditions, such as cobalt nitrate $[Co(NO_3)_2 \cdot 6H_2O]$, cobalt oxalate $[CoC_2O_4]$, cobalt hydroxide $[Co(OH)_2]$, cobalt acetate $[Co(C_2H_3O_2)_3]$, niobium hydrogen oxalate $[Nb(HC_2O_4)_5]$, niobic acid $[Nb_2O_5 \cdot XH_2O]$, etc. The admixture of the cobalt compound and niobium compound can be calcined in the form of an aqueous solution or slurry.

The cobalt niobate promoter is then admixed with vanadium and molybdenum compounds so as to form an aqueous slurry. Suitable vanadium and molybdenum compounds include oxides of vanadium and molybdenum, or compounds which form such oxides including ammonium paramolybdate [$(NH_4)_6Mo_7O_{24} \cdot 4H_2O$], molybdic acid [$MoO_3 \cdot X\ H_2O$], ammonium vanadate [$NH_4VO_3$], vanadyl oxalate [$VOC_2O_4$], etc.

The slurry is then evaporated to dryness, oven dried (80° to 200° C.) for about 4 to about 24 hours, and then calcined in a molecular oxygen-containing gas, e.g., air, at an elevated temperature, for example, in a range of about 300° to about 650° C., preferably about 400° to about 550° C., for about 0.5 to about 24 hours, preferably about 1 to about 5 hours, at a pressure similar to the initial calcination pressure. Preferably, the catalyst of the present invention is supported so as to provide for an attrition-resistant catalyst. Refractory oxides, such as alumina, silica, zirconia or mixtures thereof, such as alumina-silica, etc., are especially preferred. The supports must possess a low surface area, for example, in the range of about 0.1 to about 10 square meters per gram, preferably from about 0.2 to about 1 square meter per gram. When supports are used, the weight ratio of cobalt niobate-promoted vanadium molybdate to support can be in the range of about 1:3 to about 1:50, preferably about 1:5 to about 1:15. If a support is used, the support is coated or impregnated with the slurry containing the cobalt niobate and the vanadium and molybdenum entities before evaporation, drying and calcination. The amounts of materials used in preparing the catalyst are those amounts sufficient stoichiometrically to obtain a catalyst containing the elements in the defined amounts.

The preparation of maleic anhydride according to the process of the present invention involves passing a $C_4$ to $C_{12}$ hydrocarbon stream, preferably a $C_4$ to $C_{10}$ hydrocarbon stream, preferably containing substantial amounts of unsaturated hydrocarbons containing at least two double bonds, for example, 1,3-butadiene, cyclopentadiene, dicyclopentadiene, piperylene, isoprene, etc., together with molecular oxygen in vapor phase at elevated temperatures and elevated pressures over a fixed bed containing the novel catalyst herein.

The relative amounts of hydrocarbon and molecular oxygen can be varied over a wide range. However, in general, the mixture of hydrocarbon and molecular oxygen will contain from about 0.2 to about 2 mol percent of hydrocarbon, preferably from about 0.5 to about 1.5 mol percent of hydrocarbon. The mixture is passed over the catalyst at a weight hourly space velocity, that is hydrocarbon to catalyst, ranging from about 0.05 to about 1.0, preferably from about 0.1 to about 0.5.

Temperatures which are suitable for use in the present process are those temperatures which initiate a reaction to produce maleic anhydride and are generally from about 300° to about 500° C., preferably about 375° to about 450° C. Pressures are not critical and can be as high as about 50 pounds per square inch (345 kPa), or even higher, but in general about atmospheric pressure will suffice.

The recovery of maleic anhydride from the reaction product can be effected in any suitable manner. For example, the product can be condensed and then scrubbed with water, and the maleic anhydride recovered from the aqueous solution by evaporation and/or crystallization.

The following examples illustrate the catalyst, preparation of such catalyst and the process for producing high yields of maleic anhydride using such catalyst.

EXAMPLE I

A cobalt niobate promoter was prepared by first dissolving 11.64 grams of cobalt nitrate [$Co(NO_3)_2 \cdot 6H_2O$] in 100 milliliters of water. The solution so obtained was then added to 10.63 grams of niobium pentoxide [$Nb_2O_5$] and the resulting mixture was stirred for 15 minutes. The mixture was then transferred to an evaporating dish and heated to 90° C. to dryness, and the resulting material was calcined in air at atmospheric pressure at 900° C. for 16 hours to yield a crystalline material having the formula $CoNb_2O_6$ and an x-ray diffraction pattern with the principal peaks set forth below in Table I.

TABLE I

| d(A°) | I/I$_o$ |
|---|---|
| 3.62 | 31 |
| 2.94 | 100 |
| 2.51 | 11 |
| 2.48 | 12 |
| 1.76 | 11 |
| 1.720 | 13 |
| 1.716 | 12 |
| 1.708 | 18 |
| 1.704 | 12 |

In the above Table I, d(A°)=diameter in Angstroms, I=intensity and I$_o$=maximum intensity.

The aforesaid procedure was repeated, except that a lower calcination temperature of 550° C. was used to produce a second sample of cobalt niobate promoter in which cobalt and niobium oxides were only partially reacted to form a mixture of crystalline phases.

EXAMPLES II-VIII

For purposes of comparison, four vanadium molybdate catalysts were prepared. The first catalyst was prepared by mixing 2.04 grams of ammonium vanadate [$NH_4VO_3$] and 0.66 gram of ammonium paramolybdate [$(NH_4)_6Mo_7O_{24} \cdot 4H_2O$] in 100 milliliters of water. The mixture was stirred for 15 minutes and then transferred to an evaporating dish to which 26.35 grams of silica-alumina spheres having a surface area of about 0.75 square meter per gram were added and then mixed at 90° C. until dryness. The resultant slurry was oven dried overnight at 120° C. and then calcined in air at atmospheric pressure and a temperature of 500° C. for 2 hours. After calcining the spheres were crushed and sieved to obtain 10 to 20 mesh particles.

A titanium dioxide-promoted catalyst was prepared by repeating the aforesaid procedure, except that 2.13 grams of titanium oxide ($TiO_2$) were mixed with the ammonium vanadate, ammonium paramolybdate and water.

Two cobalt niobate-promoted catalysts were then prepared by repeating the aforesaid procedure, except that 2.13 grams of the cobalt niobate [$CoNb_2O_6$] of Example I that had been calcined at 550° C. and 2.13 grams of the cobalt niobate sample that had been calcined at 900° C., respectively, were each mixed with the ammonium vanadate, ammonium paramolybdate and water in two separate experiments to obtain two cobalt niobate promoted catalysts, each containing approximately 7.0 weight percent vanadium molybdate ($V_{4.7}MoO_{14.75}$), 7.0 weight percent cobalt niobate ($CoNb_2O_6$) and 86 weight percent silica alumina support.

Multiple tests were conducted wherein 10 grams of each catalyst as prepared above was diluted to a volume of 45 milliliters with 10 to 20 mesh quartz and charged to a ¾ inch tubular stainless steel reactor. The reactor was immersed in a fluidized alundum bath and heated to reaction temperature with air flowing over the catalyst bed. A single hydrocarbon or a mixture of hydrocarbons were then pumped into the heated line to produce a feed stream containing one mol percent hydrocarbon at a weight hourly space velocity of 0.2. After a suitable line-out period, the product was collected in a cold finger trap at −78° C. and then passed to a scrubber containing water. At the end of the run the scrubber solution was added to the cold finger trap to dissolve the maleic anhydride. The total acidity of the final solution was determined by potentiometric titration with 0.1 N NaOH. The percentage of the total acidity attributable to maleic anhydride was then determined by gas chromatagraphic analysis of the scrubber solution, and the weight percent yield was calculated.

Four hydrocarbon streams were used in the runs. Stream A contained more than 95% by weight dicyclopentadiene. Stream B contained only butadiene. Stream C had the following analysis:

| Component | Weight Percent |
|---|---|
| 2-methylbutene-2 | 20.4 |
| Piperylene | 47.7 |
| Dipentenes Plus Dicyclopentadiene | 21.8 |
| Other C5's* | 10.1 |

*Isoprene, Cyclopentadiene, Cyclopentene, Pentyne-1, Cis- and Trans-pentene-2

Stream D had the following analysis:

| Component | Weight Percent |
|---|---|
| Piperylene | 34.8 |
| Dicyclopentadiene | 30.2 |
| Cyclopentene Plus Unanalyzed C6's | 25.4 |
| Other Unanalyzed Dipentenes | 8.1 |
| Other C5's* | 1.5 |

*Isoprene, Cyclopentadiene, Cyclopentene, Pentyne-1, Cis- and Trans-pentent-2

The results obtained are set forth below in Table II.

TABLE II

| Example Nos. | Hydrocarbon Stream | Promoter | Promoter Calcination Temperature (°C.) | Bath Temperature (°C.) | Yield of Maleic Anhydride (Wt. %) |
|---|---|---|---|---|---|
| II | A | None | — | 400 | 58 |
| III | A | $TiO_2$ | — | 400 | 75 |
| IV | A | $CoNb_2O_6$ | 550 | 400 | 83 |
| V | A | $CoNb_2O_6$ | 900 | 425 | 72 |
| VI | B | $CoNb_2O_6$ | 550 | 400 | 84 |
| VII | C | $CoNb_2O_6$ | 550 | 400 | 75 |
| VIII | D | $CoNb_2O_6$ | 550 | 400 | 76 |

The results set forth in Table II show that in Example II, wherein the catalyst contained solely vanadium and molybdenum oxides, the yield of maleic anhydride was only 58 weight percent. The addition of $TiO_2$ to the catalyst, as in Example III, and in U.S. Pat. No. 4,113,745 to Strojny et al, referred to above, was sufficient to increase substantially the maleic anhydride yield to 75 weight percent. However, substitution of cobalt niobate for titanium oxide in Example V resulted in maleic anhydride yield (72 weight percent) about equivalent to that of Example III. In Example IV, the cobalt niobate promoter was calcined at 550° C., and the yield of maleic anhydride was unexpectedly increased to 83 weight percent.

In Examples VI, VII and VIII, hydrocarbon streams of differing compositions were used with the cobalt niobate promoter calcined at 550° C., and the yield of maleic anhydride was substantially increased over that in which no promoter was used with a hydrocarbon stream which was more favorable towards producing maleic anhydride.

We claim:

1. A process for preparing maleic anhydride which comprises passing a vapor mixture containing at least one $C_4$ to $C_{12}$ hydrocarbon and molecular oxygen over a catalyst comprising a cobalt niobate-promoted vanadium molybdate under reaction conditions to obtain a mixture containing maleic anhydride.

2. The process of claim 1, wherein a reaction temperature between about 300° to about 500° C. is used.

3. The process of claim 2, wherein the reaction temperature is between about 375° to about 450° C.

4. The process of claim 1, wherein the reaction pressure is between about 0 to about 50 pounds per square inch (345 kPa).

5. The process of claim 1, wherein the weight hourly space velocity, based on hydrocarbon to catalyst, is from about 0.05 to about 1.0.

6. The process of claim 5, wherein the weight hourly space velocity, based on hydrocarbon to catalyst, is from about 0.1 to about 0.5.

7. The process of claim 1, wherein the hydrocarbon stream contains at least one $C_4$ to $C_{10}$ hydrocarbon.

8. The process of claim 7, wherein the hydrocarbon stream contains substantial amounts of unsaturated hydrocarbons containing at least two double bonds.

9. The process of claim 1, wherein the mixture of hydrocarbon and molecular oxygen will contain from about 0.2 to about 2.0 mol percent of hydrocarbon.

10. The process of claim 9, wherein the mixture of hydrocarbon and molecular oxygen will contain from about 0.5 to about 1.5 mol percent of hydrocarbon.

11. The process of claim 1, wherein the cobalt niobate promoter has the formula:

$$CoNb_aO_x$$

wherein a is a number from about 1.0 to about 4.0 and x is a number from about 3.5 to about 11.0.

12. The process of claim 11, wherein a is a number from about 1.5 to about 3.0 and x is a number from about 4.5 to about 8.5.

13. The process of claim 12, wherein the cobalt niobate has the formula:

$$CoNb_2O_6$$

14. The process of claim 11, wherein the cobalt niobate promoter is calcined at 450°–700° C.

15. The process of claim 1, wherein the weight ratio of the vanadium molybdate to the cobalt niobate is from about 1:3 to about 3:1.

16. The process of claim 15, wherein the weight ratio of the vanadium molybdate to the cobalt niobate is from about 1:2 to about 2:1.

17. The process of claim 1, wherein the molar ratio of vanadium molybdenum is from about 2:1 to about 10:1.

18. The process of claim 17, wherein the molar ratio of vanadium to molybdenum is from about 3:1 to about 7:1.

19. The process of claim 1, wherein said catalyst comprises a support.

20. The process of claim 19, wherein the support is alumina, silica, zirconia or mixtures thereof.

21. The process of claim 20, wherein the support is silica-alumina.

22. The process of claim 19, wherein the support has a surface area from about 0.1 to about 10 square meters per gram.

23. The process of claim 22, wherein the support has a surface area from about 0.2 to about 1 square meter per gram.

* * * * *

UNITED STATES PATENT AND TRADEMARK OFFICE
CERTIFICATE OF CORRECTION

PATENT NO. : 4,328,157             Page 1 of 2
DATED : May 4, 1982
INVENTOR(S) : Robert A. Innes and Anthony J. Perrotta It is certified that error appears in the above-identified patent and that said Letters Patent are hereby corrected as shown below:

In the Abstract, line 16, delete "cam".

Column 2, line 64, "$[Co(No_3)_2.6H_2O]$" should read
--$[Co(No_3)_2 \cdot 6H_2O]$--;

line 67, "$[Nb_2O_5.XH_2O]$" should read
--$[Nb_2O_5 \cdot XH_2O]$--.

Column 3, line 8, "$[(NH_4)_6Mo_7O_{24}.4H_2O]$" should read
--$[(NH_4)_6Mo_7O_{24} \cdot 4H_2O]$--;

line 9, "$[MoO_3.X\ H_2O]$" should read
--$[MoO_3 \cdot X\ H_2O]$--.

UNITED STATES PATENT AND TRADEMARK OFFICE
CERTIFICATE OF CORRECTION

PATENT NO. : 4,328,157
DATED : May 4, 1982
INVENTOR(S) : Robert A. Innes and Anthony J. Perrotta It is certified that error appears in the above-identified patent and that said Letters Patent are hereby corrected as shown below:

Column 4, line 9, "$[Co(NO_3)_2.6-$" should read --$[Co(NO_3)_2 \cdot 6-$ --;

line 45, "$[(NH_4)_6Mo_7O_{24}.4H_2O]$" should read --$[(NH_4)_6Mo_7O_{24} \cdot 4H_2O]$--.

Column 5, line 48, "Trans-pentent-2" should read --Trans-pentene-2--.

Signed and Sealed this

Tenth Day of May 1983

[SEAL]

Attest:

GERALD J. MOSSINGHOFF

*Attesting Officer*  *Commissioner of Patents and Trademarks*